United States Patent
Depel

(10) Patent No.: US 9,457,164 B2
(45) Date of Patent: Oct. 4, 2016

(54) INSERT FOR TRACHEOSTOMY TUBE NECK STRAPS

(71) Applicant: TRACOE MEDICAL GmbH, Nieder-Olm (DE)

(72) Inventor: William Allen Depel, Crown Point, IN (US)

(73) Assignee: TRACOE MEDICAL GMBH, Nieder-Olm (DE)

(*) Notice: Subject to any disclaimer, the term of this patent is extended or adjusted under 35 U.S.C. 154(b) by 365 days.

(21) Appl. No.: 13/788,230

(22) Filed: Mar. 7, 2013

(65) Prior Publication Data
US 2013/0255693 A1    Oct. 3, 2013

Related U.S. Application Data

(60) Provisional application No. 61/619,067, filed on Apr. 2, 2012.

(51) Int. Cl.
*A61M 16/00* (2006.01)
*A61M 16/04* (2006.01)

(52) U.S. Cl.
CPC ..... *A61M 16/0465* (2013.01); *A61M 16/0429* (2014.02); *A61M 16/0497* (2013.01); *Y10T 29/49826* (2015.01)

(58) Field of Classification Search
CPC .......... A61M 16/04; A61M 16/0497; A61M 16/0465; A61M 16/0402
USPC ........................................ 128/207.17, 207.14
See application file for complete search history.

(56) References Cited

U.S. PATENT DOCUMENTS

| | | | | |
|---|---|---|---|---|
| 2,761,183 A | * | 9/1956 | Renno | B60J 1/14 49/144 |
| 3,930,311 A | * | 1/1976 | Andrews | 433/8 |
| 5,054,482 A | * | 10/1991 | Bales | A61M 16/0465 128/207.14 |
| 6,105,577 A | * | 8/2000 | Varner | A61M 16/0465 128/207.14 |
| 2011/0240034 A1 | * | 10/2011 | Ciccone | A61M 16/0488 128/207.17 |

* cited by examiner

*Primary Examiner* — Tan-Uyen (Jackie) T Ho
*Assistant Examiner* — Victoria Leszczak
(74) *Attorney, Agent, or Firm* — Cooper Legal Group LLC

(57) ABSTRACT

A tracheal tube arrangement includes at least one neck strap including, a deformable material. The tracheal tube arrangement further includes at least one reinforcing member integrated into the neck strap. The reinforcing member includes a first opening for receiving a tie. The reinforcing member further includes at least one reinforcement opening for receiving a portion of the deformable material for bonding the reinforcing member to the neck strap. A method of providing a tracheal tube arrangement that has at least one neck strap is also provided.

18 Claims, 8 Drawing Sheets

INSERT FOR TRACHEOSTOMY TUBE NECK STRAPS

RELATED APPLICATIONS

This application claims the benefit of U.S. Provisional Application No. 61/619,067, filed on Apr. 2, 2012, the entire disclosure of which is hereby incorporated herein by reference.

BACKGROUND OF THE INVENTION

1. Field of the Invention

The present invention relates to tracheal and/or tracheostomy tubes, or any airway management tube that includes a neck strap or retaining strap, including adult and pediatric/neonatal sizes, and in particular relates to tracheal or tracheostomy tubes having a neck strap with an opening to receive a tie.

2. Discussion of the Prior Art

Tracheal tubes are known and used to assist a patient (e.g., adult, child, infant, etc.) with breathing. In general, a tracheal tube is inserted into a trachea of the patient to provide breathing therapy. The tracheal tube is supported, for example, by a neck strap and a tie that is wrapped around the patient's neck. This tie may be made from nylon, hook and loop fasteners, foam, cotton or Dacron material (fabric), metal, or any number of materials with different properties.

The material forming the neck strap often includes a flexible/deformable material that is both comfortable to the patient and pliable/bendable to accommodate for the rounded shape of the patient's neck. However, this pliable/bendable material will sometimes lack durability and may be susceptible to cutting, shearing, and/or tearing forces exerted by the tie. In particular, the tie generally extends through an opening in the neck strap, allowing for edges of the tie to cut or tear the neck strap.

Accordingly, there is a need and it would be beneficial to fortify the neck strap, in particular, the openings of the neck strap, to provide resistance to cutting and/or tearing forces exerted by the tie upon the openings.

BRIEF DESCRIPTION OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect, the present invention provides a tracheal tube arrangement including at least one neck strap with a portion supporting a tracheal tube for extending the tracheal tube into a trachea of a patient. The neck strap prevents the tracheal tube from completely extending into the trachea. The at least one neck strap includes a deformable material. The tracheal tube arrangement further includes at least one reinforcing member integrated into the neck strap. The reinforcing member includes a first opening for receiving a tie. The reinforcing member further includes at least one reinforcement opening for receiving a portion of the deformable material for bonding the reinforcing member to the neck strap.

In accordance with another aspect, the present invention provides a tracheal tube arrangement including at least one neck strap with a portion supporting a tracheal tube for extending the tracheal tube into a trachea of a patient, the at least one neck strap including a deformable material. The neck strap has an elongated body portion extending between opposing ends. At least one reinforcing member is integrated into one of the ends of the neck strap. The reinforcing member includes a rigid material having a first opening extending through the at least one neck strap for receiving a tie. The reinforcing member further includes at least one reinforcement opening for receiving a portion of the deformable material for bonding the reinforcing member to the neck strap.

In accordance with other aspects, the present invention provides a method of providing a tracheal tube arrangement that has at least one neck strap. The method includes the steps of providing the neck strap to support a tracheal tube for extending the tracheal tube into a trachea of a patient, the at least one neck strap including at least a deformable material. The method further includes the step of providing at least one reinforcing member integrated into the neck strap. The method also includes the step of providing the reinforcing member to have at least one opening for receiving a tie.

BRIEF DESCRIPTION OF THE DRAWINGS

The foregoing and other aspects of the present invention will become apparent to those skilled in the art to which the present invention relates upon reading the following description with reference to the accompanying drawings, in which.

DETAILED DESCRIPTION OF EXAMPLE EMBODIMENTS OF THE INVENTION

Figure 1:
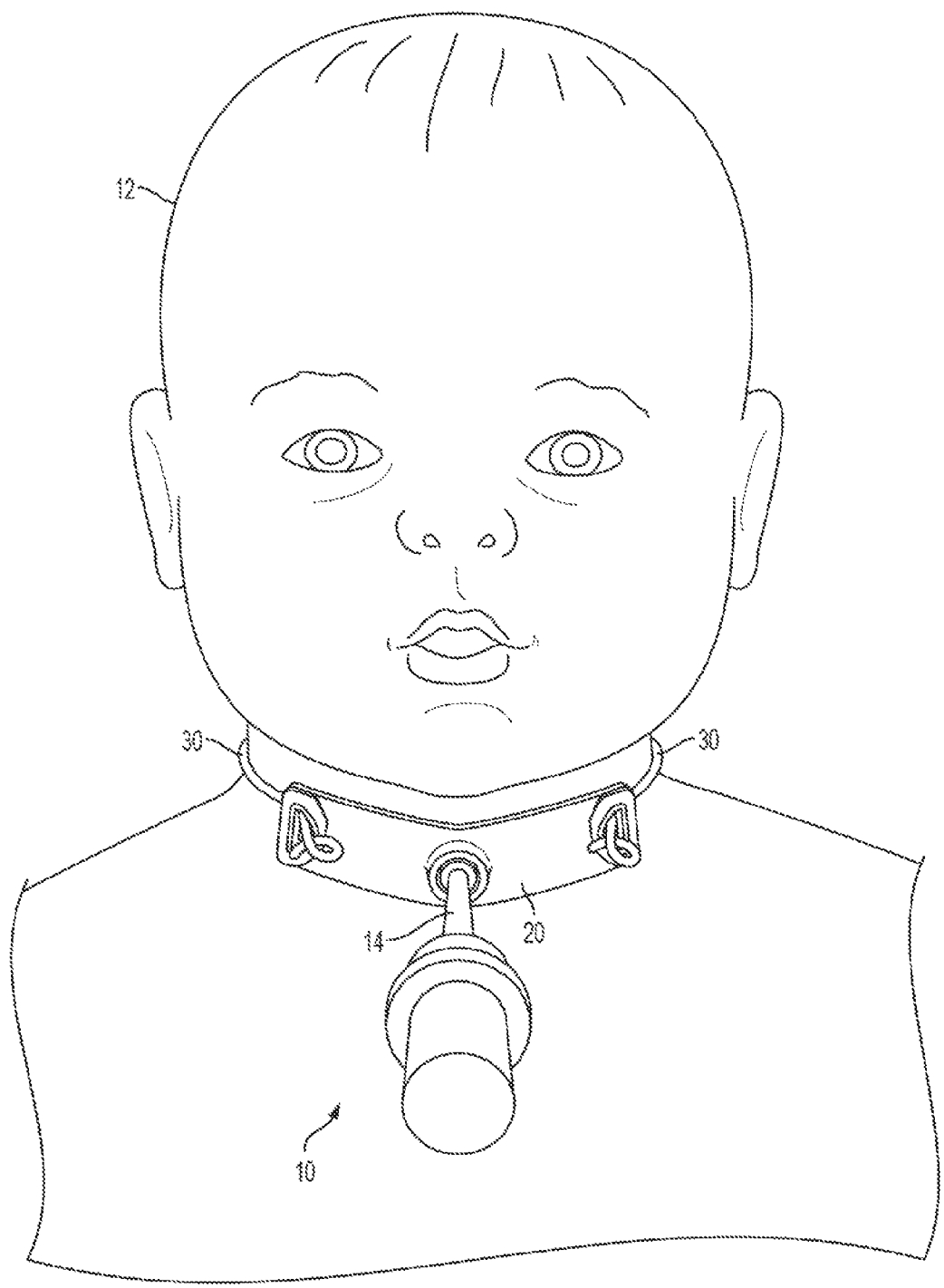
FIG. 1 is a perspective view showing an example tracheal tube arrangement that includes an example tie that extends around a neck of a patient.

Example embodiments that incorporate one or more aspects of the present invention are described and illustrated in the drawings These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

FIG. 1 shows an example tracheal tribe arrangement 10 that has been surgically applied to a patient 12 (i.e., patient representative). In short summary, the tracheal tube arrangement 10 includes a neck strap 20 secured to a neck of the patient 12 by means of a tie 30. A tracheal tube 14 extends into a trachea of the patient to provide for breathing therapy to the patient. To strengthen the neck strap 20 and reduce the likelihood of rips/tears developing due to shearing caused by the tie 30, the neck strap 20 includes a reinforcing member (discussed in detail below).

The patient 12 is depicted somewhat generically/schematically in FIG. 1. Indeed, the tracheal tube arrangement 10 can be used on patients of a wide range of sizes and ages. In some examples, the patient 12 includes infants (e.g., babies, toddlers), children, adults, and all sizes in between. While the patient 12 includes a human being in the shown example, the patient 12 is not so limited, and could also include other animals, such as mammals (e.g., primates, or the like), etc. It is to be appreciated that the tracheal tube arrangement 10 shown in FIG. 1 includes only one possible example. Indeed, in a further example, the shown tracheal tube arrangement 10 could instead be used on a child. Likewise, the shown tracheal tube arrangement 10 could also include a shorter for may not include) tracheal tube 14 on adult patients. Likewise, the tube arrangement 10 is not limited to being positioned near a patient's airway, and instead could be located at other parts of the body.

Figure 2:
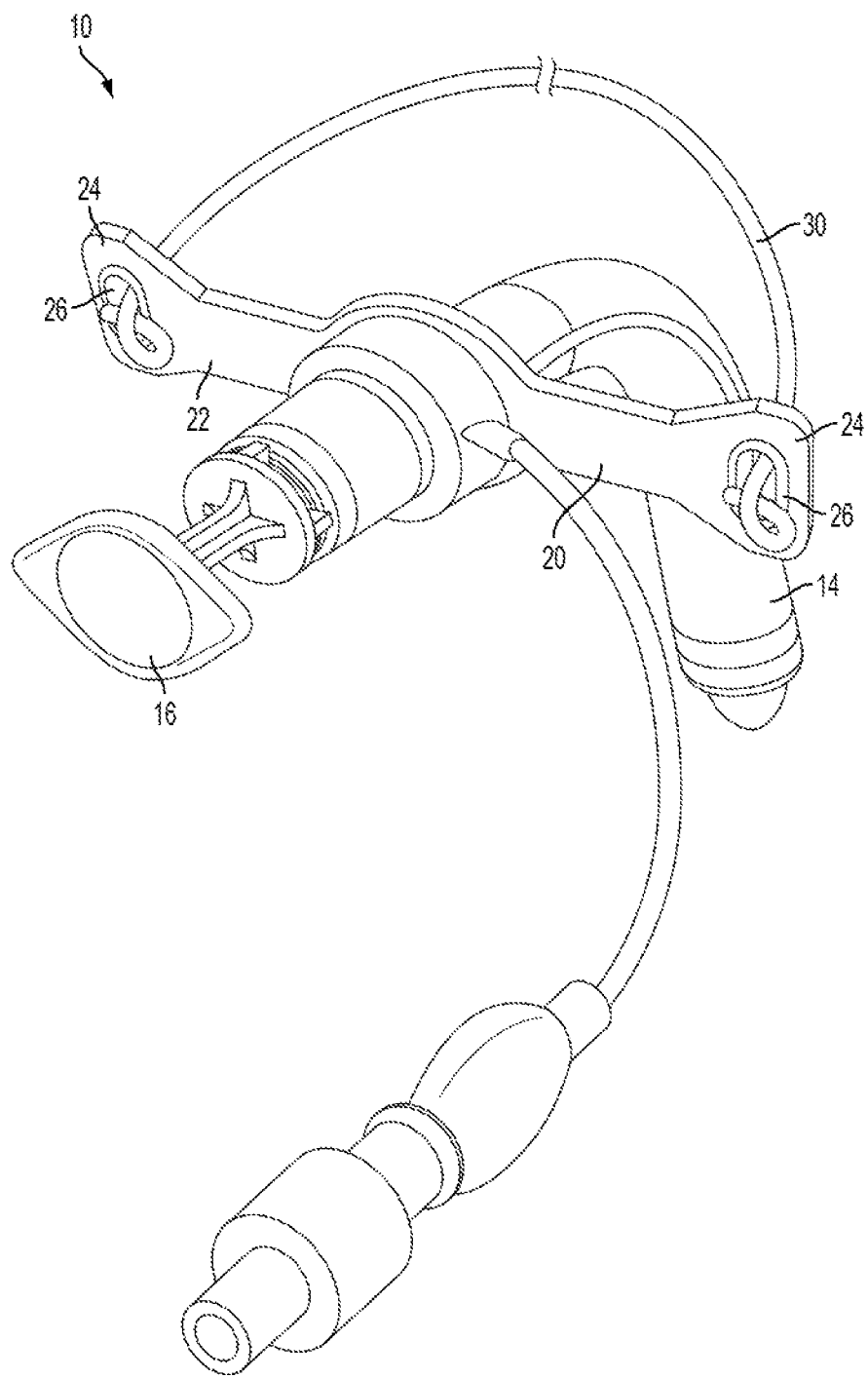
FIG. 2 is a perspective view of one example tracheal tube arrangement that includes a neck strap and the tie.

Turning now to FIG. 2, one example of the tracheal tube arrangement 10 is shown in more detail. In particular, the tracheal tube arrangement 10 is shown in a detached state from the patient 12. However, in operation (as shown in FIG. 1), the tracheal tube arrangement 10 can extend into the trachea of the patient 12 to establish and maintain an airway. It should be appreciated that extension into the trachea may occur via the oral cavity (e.g., mouth) and/or hyperpharynx as well as directly into the trachea via a tracheotomy. The tracheal tube arrangement 10 can allow for breathing and, thus, an exchange of oxygen and carbon dioxide. Also, treatments such as medical, chemical, or drug treatments can be administered through the tracheal tube arrangement 10. In general, the tracheal tube arrangement 10 provides for breathing therapy to the patient 12.

The tracheal tube arrangement 10 includes the tracheal tube 14. The tracheal tube 14 is an elongated, substantially hollow cylinder that extends into the trachea of the patient 12. The tracheal tube 14 serves as a conduit for the passage of air/gas (e.g., oxygen, carbon dioxide, etc.) to/from the breathing tube of the patient 12. The tracheal tube 14 includes a wide range of sizes and shapes, such as by being longer/shorter, straight/curved, or wider/narrower than as shown in the example.

In one example, the tracheal tube arrangement 10 includes an obturator 16. The obturator 16 is removed after tube placement and serves to provide a rigid structure for tracheal tube 14 placement.

It is to be appreciated that While the tracheal tube arrangement 10 is shown to include the tracheal tube 14 and the obturator 16, the tracheal tube arrangement 10 is not limited to including these structures. Rather, in other examples, the tracheal tube arrangement 10 may include other structures, some of which are not shown, that are generally included in tracheal tube arrangements. Indeed, in some possible structures that the tracheal tube arrangement 10 may include are cuffed/uncuffed tubes, straight/curved, reinforced (e.g., "armored") or non-reinforced tracheal tubes, obturators, additional connectors, etc. Accordingly, the tracheal tube arrangement 10 shown in FIG. 2 includes only one of many possible designs/constructions.

Turning now to the neck strap 20 of the tracheal tube arrangement 10, the neck strap 20 extends at least partially about the neck of the patient 12. In the shown example, the neck strap 20 includes an elongated body portion 22 extending between opposing ends 24. The neck strap 20 includes an opening (not visible in FIG. 2) through which the tracheal tube 14 passes. through the neck strap 20. As such, the neck strap 20 will support and/or attach to the tracheal tube 14. The neck strap 20 can prevent the tracheal tube 14 from completely extending into the patient's trachea and/or from inadvertently falling out of the patient's trachea.

The body portion 22 of the neck strap 20 extends along a generally linear axis, such that the neck strap 20 is straight. However, the neck strap 20 is not so limited to extending along the generally linear axis, and in other examples, the neck strap 20 can include bends or angles, such that the neck strap 20 extends along a non-linear axis. In one possible example, the body portion 22 of the neck strap 20 includes a V-shaped angle, though other shapes are envisioned.

In order to provide comfort to the patient 12 and compliance to the curved shape of the neck, the body portion 22 of the neck strap 20 can be made of a desirable material. In one example, the body portion 22 of the neck strap 20 includes a deformable material that is readily flexible and can flex (e.g., bend, curve, etc.) in response to a contour and shape of the patient's neck. The neck strap 20 can include, for example, a silicone material, though other materials, such as elastomeric materials, polymeric, or other soft materials that can be molded, are envisioned that may minimize irritation to the patient 12. In other examples, the body portion 22 can include an elastomeric, polymeric material or the like. The body portion 22 of the neck strap 20 can be longer or shorter in length (e.g., between the opposing ends 24) to accommodate for the various sizes of patients 12 (e.g., infant, toddler, adult, etc.).

The neck strap 20 further includes one or more openings extending therethrough. In the shown example, the body portion 22 includes a pair of strap openings 26 disposed near the ends 24 of the neck strap 20. The strap openings 26 are generally identical in size and shape to each other. In other examples, the strap openings 26 are not limited to being positioned at the ends 24, and instead could be positioned closer towards a center of the body portion 22. Likewise, the strap openings 26 may be larger or smaller than as shown, and/or could include a variety of shapes, such as circular shapes, triangular, quadrilateral shapes, shapes with rounded edges, etc.

Turning now to the tie 30 of the tracheal tube arrangement 10, the tie 30 assists in maintaining the tracheal tube arrangement 10 at a desired position with respect to the patient 12. The tie 30 is somewhat generically/schematically depicted in FIG. 2, as it is to be appreciated that the tie 30 includes any number of constructions. In one example, the tie 30 extends through each of the strap openings 26 and is secured around the neck of the patient 12 to retain the tracheal tube arrangement 10 in the desired position. The tie 30 may include various forms. In one example, the tie 30 includes a fabric ribbon. The ribbon is secured to the strap openings 26 via the use of a bow knot or the like. In another example, the tie 30 includes as hook and loop fastening arrangement, which is commonly referred to by the brand name VELCRO®. It is to be appreciated that the tie 30 could be longer or shorter than as shown to accommodate for the varying sizes of the patient 12 (e.g., infant, toddler, adult, etc.) may be constructed of nylon, foam, metal hooks, etc.

Within one example, the tie 30 may have at least one surface or edge that has a propensity to nick or cut the neck strap 20 at the edges of the openings 26. A nick, cut, or the like may lead to propagation and potentially eventual cutting through (e.g., separation) of the neck strap 20 at the location of the opening.

Figure 3:
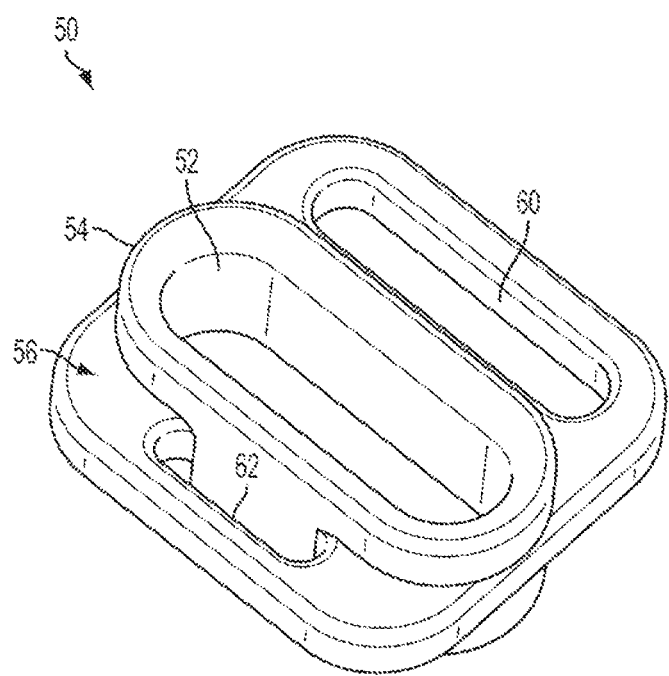
FIG. 3 is a perspective view of an example reinforcing member prior to mold-integration into the neck strap.

Turning now to FIG. 3, the tracheal tube arrangement 10 further includes at least one reinforcing member 50 for reinforcing/fortifying the openings 26 of the neck strap 20. The reinforcing member 50 is integrally molded with the neck strap 20. In one example, two reinforcing members 50 are provided, with the reinforcing members 50 being disposed at the ends 24 of the body portion 22 of the neck strap 20. It is to be appreciated that while only one reinforcing member 50 is shown in FIG. 3, the other, unshown, reinforcing member is generally identical to the shown reinforcing member 50.

The reinforcing member 50 includes a first opening 52. The first opening 52 extends through the reinforcing member 50 from one side to an opposing second side. The first opening 52 in this example is an elongated aperture with rounded, semi-circular ends. Of course, the first opening 52 is not limited to this shape, and could include any number of sizes and shapes. For example, the first opening 52 could include other quadrilateral shapes (e.g., squares, rectangles, etc.), circular/rounded shapes, triangular shapes, five or more sided geometric cross-sectional shapes, or the like. Further, the first opening 52 could be larger or smaller (e.g., longer/shorter and/or wider/narrower) than as shown.

The reinforcing member 50 includes at least one collar 54 that extends around the first opening 52. The collar 54 projects outwardly from a surface 56 of the reinforcing member 50. The collar 54 in the shown example extends around the entire perimeter of the first opening 52. In other examples, however, the collar 54 may extend around less than the entire perimeter of the first opening 52. The collar 54 can include one collar positioned on one side of the reinforcing member 50 and another collar positioned on an opposing second side of the reinforcing member 50.

The reinforcing member 50 includes a rigid or substantially rigid material. The reinforcing member 50 includes, for example, polymer, plastic, metal, nylon or the like. In one example, the reinforcing member 50 is more rigid/stiff than the neck strap 20.

The reinforcing member 50 includes at least one reinforcement opening. In the example shown in FIG. 3, the reinforcing member 50 includes a first reinforcement opening 60 and a second reinforcement opening 62. The first reinforcement opening 60 is positioned adjacent the first opening 52. In this example, the first reinforcement opening 60 is an elongated aperture with rounded, semi-circular ends. The first reinforcement opening 60 extends through the reinforcing member 50 from one side to an opposing side.

In the shown example, the first reinforcement opening 60 has a similar shape as the first opening 52, but for being slightly smaller in size (e.g., length and width). In other examples, however, the first reinforcement opening 60 is not limited to this shape, and could include other sizes and shapes. For example, the first reinforcement opening 60 could include other quadrilateral shapes (e.g., squares, rectangles, etc.), circular/rounded shapes, triangular shapes, etc. Further, the first reinforcement opening 60 could be larger or smaller (e.g., longer/shorter and/or wider/narrower) than as shown, or could include several openings.

The reinforcing member 50 further includes the second reinforcement opening 62. The second reinforcement opening 62 is positioned adjacent the first opening 52 on an opposite side from the first reinforcement opening 60. The second reinforcement opening 62 is an elongated aperture with rounded, semi-circular ends. The second reinforcement opening 62 extends through the reinforcing member 50 from one side to an opposing side.

In the shown example, the second reinforcement opening 62 is smaller in size (e.g., length and width) than both the first opening 52 and the first reinforcement opening 60. Of course, it is to be understood that the second reinforcement opening 62 is not limited to such a size, and instead could be larger or smaller (e.g., longer/shorter and/or wider/narrower) than as shown. Further, the second reinforcement opening 62 is not limited to the shape shown in FIG. 3, and in other examples, could include other quadrilateral shapes (e.g., squares, rectangles, etc.), circular/rounded shapes, triangular shapes, etc. or multiple openings. In this example, the second reinforcement opening 62 shares a wall with the first opening 52, but in other examples, the second reinforcement opening 62 could be spaced apart from the first opening 52.

Figure 4:
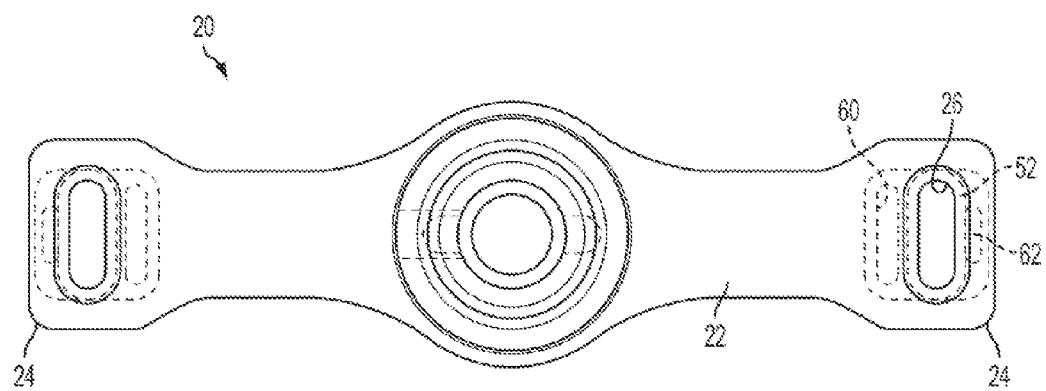
FIG. 4 is a plan view of the example reinforcing member after being mold-integrated into the neck strap.

Turning now to FIG. 4, the reinforcing member 50 is shown integrated into the neck strap 20. The reinforcing member 50 is integrally molded into the ends 24 of the neck strap 20. Initially, the flexible material forming the neck strap 20 is in a pliable or liquid state. The relatively rigid reinforcing member 50 is embedded into the pliable/liquid material forming the neck strap 20. As such, the material forming the neck strap 20 will flow around the reinforcing member 50 and into openings (e.g., first reinforcement opening 60, second reinforcement opening 62) of the reinforcing member 50. Accordingly, once the material forming the neck strap 20 solidifies, the neck strap 20 will both surround and form a mechanical bond with the reinforcing member 50, thus limiting the likelihood of the reinforcing member 50 from separating from the neck strap 20. In addition, the neck strap 20 may also form a chemical bond with the reinforcing member 50. To assist in the formation of the chemical bond, a primer material may be used on the reinforcing member 50 prior to being bonded to the neck strap 20.

As shown in FIG. 4, the reinforcing member 50 is substantially entirely integrated within the material forming the neck strap 20. Indeed, as shown, the neck strap material will flow into each of the first reinforcement opening 60 and the second reinforcement opening 62. It is to be appreciated that the first reinforcement opening 60 and second reinforcement opening 62 are embedded within the neck strap 20 and are normally not visible. However, to show the relative positions of the first reinforcement opening 60 and second reinforcement opening 62 with respect to the neck strap 20, the first reinforcement opening 60 and second reinforcement opening 62 are depicted with dashed lines. By flowing through the reinforcement openings 60, 62, the material that forms the neck strap 20 will mechanically bond with the reinforcing member 50, thus maintaining the reinforcing member 50 within the neck strap 20. As set forth above, a chemical bond may also be formed between the neck strap 20 and the reinforcing member 50.

The first opening 52 of the reinforcing member 50 is also at least partially encapsulated by the material forming the neck strap 20. In particular, the material forming the neck strap 20 will flow into and around the first opening 52. Due to the relatively larger size of the first opening 52 as compared to the reinforcement openings 60, 62, the first opening 52 will not be completely filled/closed. Instead, the material forming the neck strap 20 may cover the edges/perimeter of the first opening 52 to form the strap openings 26. As can be seen in FIG. 4, the strap openings 26 are slightly smaller in size (e.g., length and width) than the first opening 52. In other examples, however, the strap openings 26 are not limited to this size, and could be larger (so as to be closer in size to the first opening 52) or smaller than as shown. In general, the strap openings 26 will be at least large enough to allow for the tie 30 to extend there through.

Figure 5:
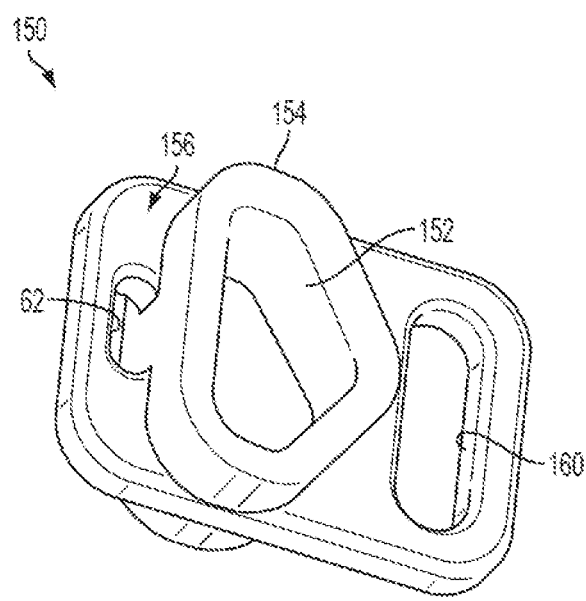
FIG. 5 is a perspective view of a second example reinforcing member prior to molding-integration into the neck strap.

Turning now to FIG. 5, an example of a second reinforcing member 150 is shown. The second reinforcing member 150 can be used in association with various tracheal tube arrangements and neck straps, including the tracheal tube arrangement 10 and neck strap 20 described above with respect to FIGS. 1 and 2. In this example, the second reinforcing member 150 is shown separate and detached from the neck strap 20 for illustrative purposes and to more clearly show features of the second reinforcing member 150. However, in operation, the second reinforcing member 150 will be integrated with the neck strap 20 in a similar manner as shown in FIG. 4.

The second reinforcing member 150 includes at least some features that are similar to the reinforcing member 50 shown in FIG. 3. For example, the second reinforcing member 150 includes the first reinforcement opening 60 and the second reinforcement opening 62. Likewise, the second reinforcing member 150 can be formed of the same materials as the reinforcing member 50. As such, these features need not be described, in detail again with respect to the second reinforcing member 150.

The second reinforcing member 150 includes a first opening 152. The first opening 152 extends through the second reinforcing member 150 from one side to an opposing second side. The first opening 152 in this example includes a five-sided geometric cross sectional area In particular, the first opening 152 may have a generally triangular shape with rounded edges. The first opening 152 is, of course, not limited to this size and shape, and in further examples, could be larger or smaller than as shown.

The second reinforcing member 150 includes at least one collar 154 that extends around the first opening 152. The collar 154 projects outwardly from a surface 156 of the second reinforcing member 150. The collar 154 in the shown example extends around the entire first opening 152. In other examples, however, the collar 154 may extend around less than all of the first opening 152. The collar 154 can include one collar positioned on one side of the second reinforcing member 150 and another collar 154 positioned on an opposing second side of the second reinforcing member 150. In this example, the collar 154 has a five-sided geometric cross sectional that matches the shape of the first opening 152. In other examples, the collar 154 is not limited to such a shape, and instead could include circular shapes, quadrilateral shapes, etc.

Figure 6:
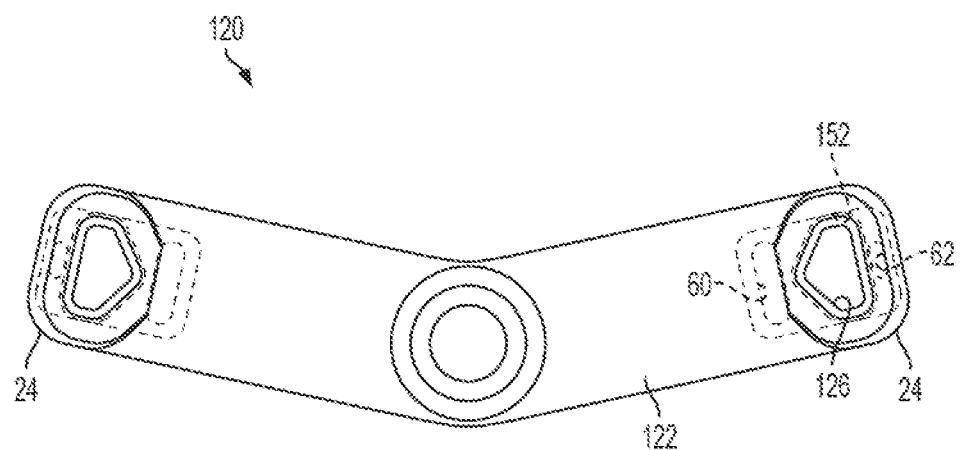
FIG. 6 is a plan view of the second example reinforcing member after being mold-integrated into a neck strap that has a shallow V-shaped angle.

Turning now to FIG. 6, the second reinforcing member 150 is shown integrated into a second example neck strap 120. It is to be noted that in this example, the second neck strap 120 is generally identical to the neck strap 20 described above but for having a body portion 122 that has a V-shaped angle. The second reinforcing member 150 is integrally molded into the ends 24 of the second neck strap 120. As set forth above, the flexible material forming the second neck strap 120 will initially be in a pliable or liquid state. The second reinforcing member 150 is embedded into the pliable/liquid material forming the second neck strap 120. As such, the material forming the second neck strap 120 flows around the second reinforcing member 150 and into the first reinforcement opening 60 and second reinforcement opening 62.

As shown in FIG. 6, the first opening 152 of the second reinforcing member 50 is also at least partially encapsulated by the material forming the second neck strap 120. In particular, the material forming the second neck strap 120 will flow into and around the first opening 152. Due to the relatively larger size of the first opening 152 as compared to the reinforcement openings 60, 62, the first opening 152 will not be completely filled/closed. Instead, the material forming the second neck strap 120 may cover the edges of the first opening 152 to form a strap opening 126 through which a tie is threaded. As shown, the strap opening 126 is slightly smaller in size than the first opening 152. In further examples, however, the strap opening 126 is not limited to this size, and could be larger or smaller than as shown. In general, the strap openings 126 will he at least large enough to allow for the tie 30 to pass there through.

Figure 7:
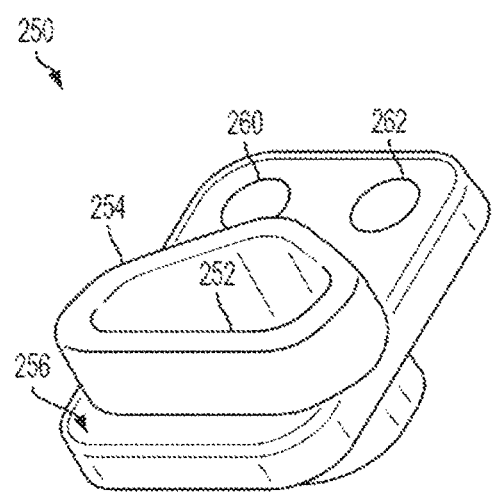
FIG. 7 is a perspective view of a third example reinforcing member prior to molding-integration into the neck strap.

Turning now to FIG. 7, an example of a third reinforcing member 250 is shown. The third reinforcing member 250 can be used in association with various tracheal tube arrangements and neck straps, including the tracheal tube arrangement 10 and neck straps 20, 120 described above with respect to FIGS. 1, 2, and 6. In this example, the third reinforcing member 250 is shown separate and detached from the neck strap 20, 120 for illustrative purposes and to more clearly show features of the third reinforcing member 250. However, in operation, the third reinforcing member 250 will be integrated with the neck strap 20, 120 in a similar manner as shown in FIG. 4 or 6.

FIG. 7 depicts only one of the third reinforcing members 250. It is to he appreciated that the other, unshown, third reinforcing member 250 is generally identical to the third reinforcing member 250 shown in the example. The third reinforcing member 250 includes a first opening 252. The first opening 252 extends through the third reinforcing member 250 from one side to an opposing second side. The first opening 252 is generically identical to the first opening 152 of the second reinforcing member 150 shown in FIG. 5 and need not be described in detail again.

The third reinforcing member 250 further includes at least one collar 254 that extends from a surface 256 around the first opening 252. The collar 254 is generally identical to the collar 154 described above with respect to the second reinforcing member 150 and need not be described again.

The third reinforcing member 250 includes at least one reinforcement opening. In the shown example, the at least one reinforcement opening includes a first reinforcement opening 260 and a second reinforcement opening 262. The first reinforcement opening 260 is generally identical in size and shape as the second reinforcement opening 262. The first reinforcement opening 260 and second reinforcement opening 262 each have a generally circular cross-sectional shape. Of course, other sizes and shapes are envisioned. For example, the reinforcement openings 260, 262 could have quadrilateral cross-sectional shapes (e.g., square, rectangular, etc.), rounded cross-sectional shapes (e.g., oval, etc.) or the like. Likewise, the first reinforcement opening 260 and second reinforcement opening 262 need not be identical in shape, as one reinforcement opening could have a different shape from the other reinforcement opening.

The reinforcement openings 260, 262 are positioned on one side of the first opening 252. The reinforcement openings 260, 262 are positioned adjacent and spaced apart from each other. It is to be appreciated that the reinforcement openings 260, 262 are not limited to the position shown in FIG. 7. Rather, in other examples, the reinforcement openings 260, 262 could be closer together or farther apart. Similarly, the reinforcement openings 260, 262 could be closer to/farther from the first opening 252. As such, the reinforcement openings 260, 262 shown in FIG. 7 include only one of many possible configurations.

In use, the third reinforcing member 250 is integrated into the neck strap 20, 120. The third reinforcing member 250 is integrally molded into ends 24 of the neck strap 20, 120. As set forth above, the flexible material forming the neck strap 20, 120 will initially flow around the third reinforcing member 250 and into the openings (e.g., first reinforcement opening 260, second reinforcement opening 262) of the third reinforcing member 250. Accordingly, once the material forming the neck strap 20, 120 solidifies, the neck strap 20, 120 will both surround and form a mechanical bond with the third reinforcing member 250, thus limiting the likelihood of the third reinforcing member 250 from separating from the neck strap 20, 120.

The first opening 252 of the third reinforcing member 250 may at least partially be encapsulated by the material forming the neck strap 20, 120. In particular, the material forming the neck strap 20, 120 will flow around the first opening 252. Similar to the example shown in FIG. 6, the strap opening 126 will be slightly smaller in size (e.g., length and width) than the first opening 252. Accordingly, the strap opening 126 is at least large enough to allow for the tie 30 to extend therethrough.

Figure 8:
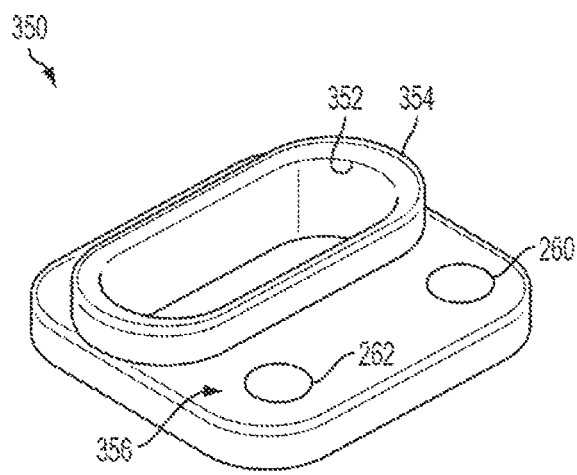
FIG. 8 is a perspective view of a fourth example reinforcing member prior to molding-integration into the neck strap.

Turning now to FIG. 8, an example of a fourth reinforcing member 350 is shown. The fourth reinforcing member 350 can be used in association with various tracheal tube arrangements and neck straps, including the tracheal tube arrangement 10 and neck strap 20, 120 described above with respect to FIGS. 1, 2 and 6. In this example, the fourth reinforcing member 350 is shown separate and detached from the neck strap 20, 120 for illustrative purposes and to more clearly show features of the fourth reinforcing member 350. However, in operation, the fourth reinforcing member 350 will be integrated with the neck strap 20, 120 in a similar manner as shown in FIG. 4 or 6. FIG. 8 depicts only one of the fourth reinforcing members 350. It is to be appreciated that the other, unshown, fourth reinforcing member 350 is generally identical to the fourth reinforcing member 350 shown in the example.

The fourth reinforcing member 350 includes the first reinforcement opening 260 and the second reinforcement opening 262. The first reinforcement opening 260 and second reinforcement opening 262 are generally identical to the first reinforcement opening 260 and second reinforcement opening 262 described above with respect to FIG. 7. As such, these features need not be described in detail again.

The fourth reinforcing member 350 includes a first opening 352. The first opening 352 can be similar or identical to the first opening 52 of the reinforcing member 50 shown in FIG. 3. In particular, the first opening 352 is an elongated aperture with rounded, semi-circular ends. The first opening 352 is, of course, not limited to this shape, and could include any number of sizes (e.g., larger or smaller than as shown) and shapes.

The first opening 352 includes at least one collar 354 that extends around the first opening 352. The collar 354 projects outwardly from a surface 356 of the reinforcing member 350. The collar 354 in the shown example extends around the entire first opening 352, though in other examples, the collar 354 could extend around less than all of the first opening 352.

In use, the fourth reinforcing member 350 is integrated into the neck strap 20, 120. The fourth reinforcing member 350 is integrally molded into ends 24 of the neck strap 20, 120. As set forth above, the flexible material forming the neck strap 20, 120 will initially flow into the first reinforcement opening 260 and second reinforcement opening 262. Accordingly, once the material forming the neck strap 20, 120 solidifies, the neck strap 20, 120 will both surround and form a mechanical bond with the fourth reinforcing member 350, thus limiting the likelihood of the fourth reinforcing member 350 from separating from the neck strap 20, 120.

The first opening 352 may at least partially be encapsulated by the material forming the neck strap 20, 120. Indeed, as set forth above with respect to FIG. 4, the strap opening 26 is formed by the material forming the neck strap 20, 120 flowing through the first opening 352. The strap opening 26 will be slightly smaller in size (e.g., length and width) than the first opening 352. Accordingly, the strap opening 26 is at least large enough to allow for the tie 30 to extend therethrough.

By providing the neck strap 20, 120 with the reinforcing members 50, 150, 250, 350, the risk of tearing and/or cutting of the neck strap 20, 120 is reduced or eliminated. In particular, the reinforcing members 50, 150, 250, 350 are mechanically bonded and integrated with the neck strap 20, 120, thus limiting the likelihood of the reinforcing members 50, 150, 250. 350 from becoming separated from the neck strap 20, 120. In addition, the reinforcing members 50, 150, 250, 350 are integrated and formed with the strap openings 26, 126. As such, the reinforcing members 50, 150, 250, 350 will also reduce the likelihood of the tie 30 from shearing and/or cutting through the strap openings 26, 126. In particular, the reinforcing members 50, 150, 250, 350 include a relatively strong, rigid material. The first opening 52, 152, 252. 352 will bound the strap openings 26, 126, thus limiting the tie 30 (which can be made of various sharp materials) from cutting/tearing through the strap openings 26, 126 due to the strong, rigid material forming the reinforcing members 50, 150, 250, 350.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. A tracheal tube arrangement including:
   at least one neck strap with a portion supporting a tracheal tube, with the tracheal tube penetrating through the at least one neck strap from a first side of at least one side of the neck strap to a second side of the at least one neck strap, for extending the tracheal tube into a trachea of a patient and for preventing the tracheal tube from completely extending into the trachea, the at least one neck strap including a deformable silicone material, with the tracheal tube penetrating through the deformable silicone material from the first side of the neck strap to the second side of the neck strap; and
   at least one reinforcing member, made of different material than the deformable silicone material, mold-integrated and non-removably embedded into the deformable silicone material of the at least one neck strap, each of the at least one reinforcing member including a first opening for receiving a tie, with the first opening penetrating through the at least one reinforcing member and penetrating through the deformable silicone material from the first side of the neck strap to the second side of the neck strap permitting the tie to extend through the at least one reinforcing member and through the deformable silicone material from the first side of the neck strap to the second side of the neck strap, the at least one reinforcing member further including at least one reinforcement opening, separate from and non-conjoined with the first opening, that receives a portion of the deformable material to bond the at least one reinforcing member to the deformable material of the at least one neck strap.

2. The tracheal tube arrangement of claim 1, wherein the at least one reinforcement opening includes a first reinforcement opening and a second reinforcement opening.

3. The tracheal tube arrangement of claim 2, wherein the first reinforcement opening is positioned on an opposite side of the first opening than the second reinforcement opening.

4. The tracheal tube arrangement of claim 2, wherein the first reinforcement opening and second reinforcement opening are positioned on a same side of the first opening.

5. The tracheal tube arrangement of claim 4, wherein the first reinforcement opening and second reinforcement opening are positioned adjacent each other.

6. A tracheal tube arrangement including:
   at least one neck strap with a portion supporting a tracheal tube for extending the tracheal tube into a trachea of a patient and for preventing the tracheal tube from completely extending into the trachea, the at least one neck strap including a deformable material: and
   at least one member non-removably embedded into the deformable material of the at least one neck strap, the at least one reinforcing member including a first opening for receiving a tie, the at least one reinforcing member further including at least one reinforcement opening that receives a portion of the deformable material to bond the at least one reinforcing member to the deformable material of the at least one neck strap;
   wherein the first opening is bounded by an outwardly projecting collar that extends outwardly from a surface of the at least one reinforcing member.

7. The tracheal tube arrangement of claim 1, wherein the first opening includes an elongated oval shape with rounded ends.

8. The tracheal tube arrangement of claim 1, wherein the first opening is triangularly shaped with rounded edges.

9. The tracheal tube arrangement of claim 1, wherein the at least one reinforcing member includes at least one of nylon polymer and metal.

10. The tracheal tube arrangement of claim 1, wherein the at .east one neck strap includes a V-shaped angle.

11. The tracheal tube arrangement of claim 6, wherein the at least one reinforcement opening includes a first reinforcement opening and a second reinforcement opening.

12. The tracheal tube arrangement of claim 11, wherein the first reinforcement opening is positioned on an opposite side of the first opening than the second reinforcement opening.

13. The tracheal tube arrangement of claim 11, wherein the first reinforcement opening and second reinforcement opening are positioned on a same side of the first opening.

14. The tracheal tube arrangement of claim 13, wherein the first reinforcement opening and second reinforcement opening are positioned adjacent each other.

15. The tracheal tube arrangement of claim 6, wherein the first opening includes an elongated oval shape with rounded ends.

16. The tracheal tube arrangement of claim 6, wherein the at least one neck strap includes one of a silicone material, elastomeric material, or polymeric conformable material as the deformable material into which the at least one reinforcing member is non-removably embedded.

17. A method of providing a tracheal tube arrangement that has at least one neck strap, the method including the steps of:
   providing the at least one neck strap to support a tracheal tube, with the tracheal tube penetrating through the at least one neck strap from a first side of at least one side of the neck strap to a second side of the at least one neck strap, for extending the tracheal tube into a trachea of a patient, the at least one neck strap including at least a deformable silicone material, with the tracheal tube penetrating through the deformable silicone material from the first side of the neck strap to the second side of the neck strap;
   providing at least one reinforcing member, made of different material than the deformable silicone material, mold-integrated and non-removably embedded into the deformable silicone material of the at least one neck strap; and
   providing each of the at least one reinforcing member to have at least one first opening for receiving a tie, with the at least one first opening penetrating through the at least one reinforcing member and penetrating through the deformable silicone material from the first side of the neck strap to the second side of the neck strap permitting the tie to extend through the at least one reinforcing member and through the deformable silicone material from the first side of the neck strap to the second side of the neck strap, the at least one reinforcing member further including at least one reinforcement opening, separate from and non-conjoined with the at least one first opening, that receives a portion of the deformable material to bond the at least one reinforcing member to the deformable material of the at least one neck strap.

18. The method of claim 17, wherein the at least one reinforcing member is provided to include at least one of nylon or metal material or other hard material.

* * * * *

UNITED STATES PATENT AND TRADEMARK OFFICE
CERTIFICATE OF CORRECTION

PATENT NO. : 9,457,164 B2
APPLICATION NO. : 13/788230
DATED : October 4, 2016
INVENTOR(S) : William Allen Depel Page 1 of 1

It is certified that error appears in the above-identified patent and that said Letters Patent is hereby corrected as shown below:

In the Claims

Column 11, Line 46, Please delete ".east" and insert therefor --least--.

Signed and Sealed this
Third Day of January, 2017

Michelle K. Lee
*Director of the United States Patent and Trademark Office*